United States Patent
Knott et al.

(10) Patent No.: US 10,399,998 B2
(45) Date of Patent: Sep. 3, 2019

(54) MIXTURES OF CYCLIC BRANCHED SILOXANES OF THE D/T TYPE AND CONVERSION PRODUCTS THEREOF

(71) Applicant: Evonik Degussa GmbH, Essen (DE)

(72) Inventors: Wilfried Knott, Essen (DE); Horst Dudzik, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/923,552

(22) Filed: Mar. 16, 2018

(65) Prior Publication Data

US 2018/0319823 A1 Nov. 8, 2018

(30) Foreign Application Priority Data

May 8, 2017 (EP) .................... 17169876

(51) Int. Cl.
| | | |
|---|---|---|
| *C07F 7/21* | (2006.01) | |
| *C07F 7/08* | (2006.01) | |
| *C08G 77/06* | (2006.01) | |
| *C08G 77/10* | (2006.01) | |
| *C08G 77/18* | (2006.01) | |
| *C08L 83/04* | (2006.01) | |
| *C08G 77/16* | (2006.01) | |

(52) U.S. Cl.
CPC ............. *C07F 7/21* (2013.01); *C07F 7/0896* (2013.01); *C08G 77/06* (2013.01); *C08G 77/10* (2013.01); *C08G 77/18* (2013.01); *C08L 83/04* (2013.01); *C08G 77/16* (2013.01)

(58) Field of Classification Search
None
See application file for complete search history.

(56) References Cited

U.S. PATENT DOCUMENTS

| | | | |
|---|---|---|---|
| 2,758,124 A | 8/1956 | Schwenker | |
| 4,613,208 A | 12/1986 | Westall | |
| 5,625,024 A | 4/1997 | Schlitte et al. | |
| 6,730,749 B1 | 5/2004 | Burkhart et al. | |
| 6,790,451 B2 | 9/2004 | Nakanishi | |
| 7,504,467 B2 | 3/2009 | Ochs | |
| 8,598,295 B2 | 12/2013 | Henning et al. | |
| 9,527,959 B2 * | 12/2016 | Byrne | C08F 10/00 |
| 9,896,541 B2 | 2/2018 | Fiedel et al. | |
| 2010/0249339 A1* | 9/2010 | Henning | C08G 77/08 525/479 |
| 2012/0168664 A1* | 7/2012 | Maurer | C08G 77/38 252/8.57 |
| 2013/0245304 A1 | 9/2013 | Schubert et al. | |
| 2016/0130290 A1 | 5/2016 | Knott et al. | |
| 2017/0081469 A1 | 3/2017 | Fiedel et al. | |
| 2017/0198099 A1 | 7/2017 | Knott | |
| 2017/0226285 A1 | 8/2017 | Lobert et al. | |
| 2018/0016392 A1 | 1/2018 | Lobert et al. | |

FOREIGN PATENT DOCUMENTS

| | | |
|---|---|---|
| DE | 3716372 A1 | 11/1988 |
| DE | 102005004676 A1 | 8/2006 |
| EP | 0381318 A2 | 8/1990 |
| EP | 0675151 A1 | 10/1995 |
| EP | 0967236 A1 | 12/1999 |
| EP | 1717260 A1 | 11/2006 |
| WO | 2009065644 A1 | 5/2009 |

OTHER PUBLICATIONS

Amajjahe et al., U.S. Appl. No. 15/760,320, filed Mar. 15, 2018.
Amajjahe et al., U.S. Appl. No. 15/760,855, filed Mar. 16, 2018.
Knott et al., U.S. Appl. No. 15/719,775, filed Sep. 29, 2017.

\* cited by examiner

*Primary Examiner* — Clinton A Brooks
*Assistant Examiner* — Kofi Adzamli
(74) *Attorney, Agent, or Firm* — Philip P. McCann; Nexsen Pruet PLLC

(57) ABSTRACT

Mixtures of cyclic branched siloxanes having exclusively D and T units, with the proviso that the cumulative proportion of the D and T units having Si-alkoxy and/or SiOH groups that are present in the siloxane matrix, determinable by $^{29}Si$ NMR spectroscopy, is greater than 2 and less than 10 mole percent, are described, as are branched organomodified siloxanes obtainable therefrom.

20 Claims, No Drawings

MIXTURES OF CYCLIC BRANCHED SILOXANES OF THE D/T TYPE AND CONVERSION PRODUCTS THEREOF

This application claims the benefit of European Application No. 17169876.4 filed on May 8, 2017, the disclosure of which is expressly incorporated herein by reference.

FIELD

The invention relates to a process for preparing cyclic branched siloxanes of the D/T type, to the cyclic branched siloxanes of the D/T type themselves, and to the methods of processing these siloxanes to give functionalized branched siloxanes and/or branched silicone oils.

BACKGROUND

Cited as a reference in relation to the M, D, T, Q nomenclature used in the context of this document to describe the structural units of organopolysiloxanes is W. Noll, Chemie and Technologie der Silicone [Chemistry and Technology of the Silicones], Verlag Chemie GmbH, Weinheim (1960), page 2 ff.

In the preparation of organomodified siloxanes, especially branched function-bearing siloxanes, a difficulty frequently encountered is that competing processes that take place simultaneously in the reaction matrix can adversely affect the quality of the desired product.

Condensation and equilibration are among these competing processes, which have to be considered separately according to the synthetic problem. A great challenge is the homogeneous distribution of branching sites along a siloxane chain (avoidance of T-structured domains). As can be inferred from the literature, the breakup of homologous siloxane chains consisting of T units under acid catalysis in particular is difficult and hence in effect cannot be accomplished in the presence of sensitive functional groups. With regard to the reactivity characteristics of M, D and T units, reference is made to M. A. Brook, "Silicon in Organic, Organometallic and Polymer Chemistry", John Wiley & Sons, Inc., New York (2000), p. 264 ff.

Especially in the preparation of branched siloxanes bearing reactive SiH groups, considerable efforts should therefore always be made to reconcile the demand for uniform distribution of siloxane units as far as possible in a statistical manner with the demand for very substantial retention of the valuable silicon-bonded hydrogen.

Polyorganosiloxanes are prepared according to the prior art by hydrolysis and condensation proceeding from methylchlorohydrosilanes having mixed substitution. Direct hydrolytic condensation of hydrogen-containing silanes, for example dimethylmonochlorosilane or methyldichlorosilane, is described, for example, in U.S. Pat. No. 2,758,124. In this case, the siloxane phase that separates in the hydrolysis is separated from the water phase having a hydrochloric acid content. Since this process is prone to gelation of the hydrosiloxanes, DE 11 25 180 describes an improved process utilizing an organic auxiliary phase, in which the hydrosiloxane formed is present as a separate phase dissolved in an organic solvent and, after separation from the acidic water phase and distillative removal of the solvent, is resistant to gelation. A further process improvement with regard to minimized solvent input is described by EP 0 967 236, the teaching of which involves first using only small amounts of water in the hydrolytic condensation of the organochlorosilanes, such that hydrogen chloride is driven out in gaseous form in the first step and can be sent directly to further end uses as a material of value.

Branched organomodified polysiloxanes can be described by a multitude of structures. In general, a distinction has to be made between a branch or crosslink which is introduced via the organic substituents and a branch or crosslink within the silicone chain. Organic crosslinkers for linkage of siloxane skeletons bearing SiH groups are, for example, α,ω-unsaturated diolefins, divinyl compounds or diallyl compounds, as described, for example, in U.S. Pat. No. 6,730,749 or EP 0 381 318. This crosslinking by platinum-catalysed hydrosilylation downstream of the equilibration means an additional process step in which both intramolecular linkages and intermolecular linkages can take place. The product properties are additionally greatly affected by the different reactivities of the low molecular weight organic difunctional compounds that have a tendency to peroxide formation.

Multiple crosslinking of the silicone block of an organomodified polysiloxane with the organic block copolymer can be effected in various ways. EP 0 675 151 describes the preparation of a polyethersiloxane by hydrosilylation of a hydrosiloxane with a deficiency of hydroxy-functional allyl polyether, in which unconverted SiH functions are joined to the hydroxyl groups of the polyether substituents via an SiOC bond with addition of sodium methoxide. The increase in molar mass leads to broad scatter in the product properties, for example the viscosity. A similar approach to the formation of branched systems is described by U.S. Pat. No. 4,631,208, in which hydroxy-functional polyethersiloxanes are crosslinked by means of trialkoxysilanes. Both methods lead to intermolecular crosslinking of the polyethersiloxanes where it is not only difficult to control the increase in molar mass but where there are also associated unpredictable rises in viscosity. Following the aforementioned methods, what is obtained is not branching within the siloxane portion at constant molar mass, but crosslinking to give macromolecular multiblock copolymers.

Branching within the siloxane chain therefore already has to be effected in the course of production of the hydrosiloxane, in order to get round the described disadvantages of the crosslinking. Branches within the siloxane chain require the synthetic incorporation of trifunctional silanes, for example trichlorosilanes or trialkoxysilanes.

As known to the person skilled in the art, the rate of hydrolysis of the organochlorosilanes rises in the following series (C. Eaborn, Organosilicon Compounds, Butterworths Scientific Publications, London 1960, p. 179):

$SiCl_4 > RSiCl_3 \gg R_2SiCl_2 > R_3SiCl$.

Therefore, in the hydrolysis and condensation reactions of trichlorosilanes, there is an elevated tendency to formation of highly crosslinked gels compared to the slower hydrolysis and condensation reactions of difunctional and monofunctional organochlorosilanes. The established processes for hydrolysis and condensation of dichloro- and monochlorosilanes are therefore not directly applicable to trichlorosilanes; instead, it is necessary to take indirect routes via multistage processes.

Building on this finding, it is also necessary to conduct the preparation of singly branched hydrosiloxanes by incorporation of not more than one trifunctional monomer per siloxane chain in a two-stage process according to the prior art. In a first step, a trifunctional low molecular weight hydrosiloxane is prepared by hydrolysis and condensation from 1,1,3,3-tetramethyldisiloxane and methyltriethoxysilane, as taught, for example, by DE 37 16 372. Only in a second step is equilibration then possible with cyclic siloxanes to give higher molar masses, as explained by DE 10 2005 004676. For further conversion—and therefore only in a third step—the singly branched hydrosiloxane thus prepared can be provided by the methods known per se for functionalization of siloxane compounds having SiH groups with organic substituents.

For synthesis of multiply branched hydrosiloxanes which, by definition, have more than one trifunctional monomer per siloxane chain, there are likewise two-stage syntheses in the prior art. In principle, it is possible to proceed from hydrosiloxanes and to subject the SiH functions, with addition of water and precious metal catalyst, to dehydrogenative conversion to silanols which are then condensed in turn with hydrosiloxanes. This procedure is described in U.S. Pat. No. 6,790,451 and in EP 1 717 260. Quite apart from the costs of the precious metal catalysis, the poor storage stability of the silanols, which have a tendency to autocondensation, makes it difficult to accomplish a reproducible, controlled process regime.

A further option described in U.S. Pat. No. 6,790,451 is that of preparing a copolymer from trichloromethylsilane or trialkoxymethylsilane with hexamethyldisiloxane or trimethylchlorosilane, also called MT polymer therein, which is equilibrated in a second step together with a polydimethyl (methylhydro)siloxane copolymer. The preparation of such MT polymers entails the use of strong bases or strong acids, in some cases in combination with high reaction temperatures, and results in prepolymers of such high viscosity that the neutralization thereof is made considerably more difficult and hence further processing to give end products of constant composition and quality is significantly limited.

According to EP 0 675 151, first of all, the hydrolysis and condensation of the SiH-free branched silicone polymer is conducted in xylene in such a way that the final occlusion of the precondensate is conducted with a large excess of hexamethyldisiloxane and, in the second step, the equilibration is undertaken with methylhydropolysiloxane to give a branched hydrosiloxane (preparation method 6, ibid.). As an alternative, the teaching of EP 0 675 151 relates to a procedure for preparation of non-SiH-functional branched siloxanes including merely a partial condensation of the methyltrichlorosilane used (preparation method 7, ibid.). However, these two procedural strategies do not address the need for a universally utilizable preparation method for branched siloxanes.

WO2009065644 A1 teaches a process for preparing branched SiH-functional siloxanes by reacting a mixture comprising
a) one or more SiH-functional siloxanes, b) one or more SiH function-free siloxanes and c) one or more trialkoxysilanes with addition of water and in the presence of at least one Brønsted-acidic catalyst, wherein the reaction is conducted in one process step. The technical limits of this process become clear from the disclosure therein with regard to the conservation of the SiH functionality introduced into the system. This shows the need to work with at least two acidic catalysts (trifluoromethanesulfonic acid vs. trifluoromethanesulfonic acid and sulfonic acid ion exchange resin, ibid. examples 5 and 6) for sensitive SiH-functional branched siloxane structures, which makes the process extremely inconvenient and costly in terms of its industrial implementation.

There has already been speculation in the literature about the possible existence of siloxanes formed exclusively from D and T units. As stated by W. Noll in Chemie and Technologie der Silicone, Weinheim (1960), page 182, D.

W. Scott (J. Am. Chem. Soc. 68, 356, 1946) was the first to suggest that bicyclic compounds of siloxanes having D and T units derive from an extremely dilute co-hydrolysis of dimethyldichlorosilane and methyltrichlorosilane with subsequent thermal rearrangement. It was possible to isolate isomers in amounts of not even 1% from the viscous co-hydrolysate at bottom temperatures between 350 and 600° C., and they were then described by cryoscopic and elemental analysis with very high levels of uncertainty. Scott speculates that his compounds having D-T structures contain T structural elements joined directly to one another and not via D units. The interpretation of the results in Scott is based on the premise that all the SiC bonds present in the co-hydrolysate withstand the severe thermal treatment that he chose.

Makarova et al. (Polyhedron Vol. 2, No. 4, 257-260 (1983)) prepared 10 oligomeric methylsiloxanes having cyclic and linear segments by the controlled low-temperature condensation of siloxanes having SiOH groups and containing SiCl groups in the presence of organic amines such as triethylamine or aniline in benzene or diethyl ether as solvents, separated off the precipitated amine hydrochlorides, and washed and then fractionally distilled the crude reaction products. Subsequently, the bicyclic methylsiloxanes were subjected to pyrolysis at temperatures between 400 and 600° C., and the pyrolysis products were characterized by gas chromatography. The low molecular weight compounds used in the course of this study, for example hydroxynonamethylcyclopentasiloxane, hydroxyheptamethylcyclotetrasiloxane, dihydroxytetramethyldisiloxane, from the point of view of the silicone chemistry conducted on the industrial scale, are to be considered as exotic species of purely academic interest.

More particularly, the pure-chain siloxane compounds of the D/T type defined in terms of molar mass that have been synthesized by this route are unsuitable for the production of organomodified siloxanes that are employed in demanding industrial applications, for example in PU foam stabilization or in the defoaming of fuels, etc. Active ingredients that effectively address such a field of use are always characterized by a broad oligomer distribution comprising high, moderate and low molar masses, since the oligomers present therein, depending on their molar mass and hence their diffusion characteristics, can very commonly be imputed to have differentiated surfactant tasks in different time windows of the respective process. Specifically in the case of the branched organomodified siloxanes, due to the reaction characteristics of M, D and T units that have been discussed at the outset, however, a good oligomer distribution combined with a uniform distribution of siloxane units in a statistical manner as far as possible in the individual molecules can only be achieved when the starting material of the D/T type used already itself conforms to a distribution function. This is all the more true when the organomodification is effected via an intermediate bearing SiH groups.

Acknowledging this prior art, there is no apparent real solution for preparation of branched organomodified siloxanes.

The as yet unpublished European patent application number 17156421.4 is geared to a preparation process for obtaining branched organomodified siloxanes, which comprises (a) in a first step preparing cyclic branched siloxanes of the D/T type by the reaction of trialkoxysilane exclusively with siloxane cycles and/or α,ω-dihydroxypolydimethylsiloxane in a solvent and (b) in a second step undertaking the functionalization of these cyclic branched siloxanes by acidic equilibration with functional silanes and/or siloxanes.

The mixtures of cyclic branched siloxanes having exclusively D and T units and having no functional groups that arise from the first step, according to that document, are characterized in that the cumulative proportion of the D and T units having Si-alkoxy and SiOH groups that are present in the siloxane matrix, determinable by $^{29}$Si NMR spectroscopy, is less than or equal to 2 mole percent, and so no significant proportions of the Si-alkoxy or SiOH groups that originate from the first stage are carried through into the second step and molecularly conserved. For this purpose, according to that document, in the first step, silicon-free solvents including liquid (alkyl)aromatics, for example toluene, the isomeric xylenes, cycloaliphatics, for example cyclohexane, but also diethyl carbonate, are used, more preferably toluene. The process disclosed in patent application number 17156421.4 opens up access in a simple manner, via the intermediate stage of the DT siloxanes, to function-bearing branched siloxanes or else to branched silicone oils. Under the aspect of technical interpretation, in that process, however, the necessity of the use of solvent such as toluene in particular can possibly be regarded as a drawback, since, in the environment of a production operation preparing specifically organomodified siloxanes, the organic auxiliary phase is always a more or less disagreeable extraneous phase, for example with regard to the removal, purification and recycling thereof into the overall process. Assurance of non-cross-contaminated streams of matter, in addition to aspects of safe storage, handling and disposal, is of particular significance.

SUMMARY

Accordingly, an important technical challenge is to enable the provision of branched organomodified siloxanes without the use of silicon-free solvents as well.

Astonishingly, it has now been found in the context of the present invention that a process comprising the acid-catalysed equilibration of trialkoxysilanes with siloxane cycles and/or α,ω-dihydroxypolydimethylsiloxane and the hydrolysis and condensation reaction initiated by addition of water, with use of simple siloxane cycles as solvents, and preferably thermal removal of the alcohol released and water present in the system and neutralization or removal of the acidic catalyst enables the preparation of mixtures of cyclic branched siloxanes. These cyclic branched siloxanes can be acid-equilibrated in a further step with silanes and/or siloxanes, especially with functional silanes and/or siloxanes, in order to obtain branched organomodified siloxanes or branched silicone oils.

This gives rise to the following items of subject-matter of the invention.

DETAILED DESCRIPTION

The invention provides mixtures of cyclic branched siloxanes having exclusively D and T units, with the proviso that the cumulative proportion of the D and T units having Si-alkoxy and/or SiOH groups that are present in the siloxane matrix, determinable by $^{29}$Si NMR spectroscopy, is greater than 2 and less than 10 mole percent, preferably less than 9 mole percent. The siloxanes do not have any further functional groups.

A particular, additional advantage of the invention is that the mixtures of the invention feature excellent storage stability, even in the case of storage under air and at high temperatures. Solidification or even through-curing does not occur, even after storage under air at elevated temperatures for a number of months.

The invention further provides mixtures of cyclically branched siloxanes having exclusively D and T units, preferably according to any of Claims 1 to 5, dissolved in a silicon-containing solvent, preferably in the isomeric siloxane cycles octamethylcyclotetrasiloxane ($D_4$), decamethylcyclotetrasiloxane ($D_5$) and/or mixtures thereof.

The invention further provides a process for preparing mixtures of cyclic branched siloxanes having exclusively D and T units, preferably according to any of Claims 1 to 5, comprising
 (a) an acid-catalysed equilibration of trialkoxysilanes with siloxane cycles and/or α,ω-dihydroxypolydimethylsiloxane in the presence of at least one acidic catalyst and then
 (b) a hydrolysis and condensation reaction initiated by addition of water, and addition of a silicon-containing solvent, followed by
 (c) a distillative removal of the alcohol released, of water present in the system and of silicon-containing solvent, and a neutralization or removal of the acidic catalyst and optionally removal of salts that have possibly formed,
 wherein the silicon-containing solvent preferably comprises the isomeric siloxane cycles octamethylcyclotetrasiloxane ($D_4$), decamethylcyclotetrasiloxane ($D_5$) and/or mixtures thereof, advantageously working in mass ratios of silicon-containing solvent to the siloxane having D and T units of 1:1 to 5:1.

The invention still further provides a process for preparing branched organomodified siloxanes, wherein in a first step cyclic branched siloxanes are provided, preferably mixtures of cyclic branched siloxanes having exclusively D and T units, with the proviso that the cumulative proportion of the D and T units having Si-alkoxy and/or SiOH groups that are present in the siloxane matrix, which is determinable by $^{29}$Si NMR spectroscopy, is greater than 2 and less than 10 mole percent, preferably less than 9 mole percent,
 and in a second step the cyclic branched siloxanes are equilibrated under acidic conditions with silanes and/or siloxanes.

The invention and its subject matter are more particularly elucidated hereinafter.

In the inventive mixtures of cyclic branched siloxanes having exclusively D and T units, in the context of a preferred embodiment of the invention, the ratio of D to T units is between 10:1 and 3:1, preferably between 6:1 and 4:1.

In a further preferred embodiment of the invention, the molar mass ratio $M_w/M_n$ of the mixture is in the range of $2<M_w/M_n<50$. These parameters can be determined from toluenic solutions of the siloxanes by gel permeation chromatography (GPC), which, with utilization of a refractive index detector, by comparison with a polystyrene standard, permits the determination of the mean molar mass $M_w$ thereof and the molar mass distribution $M_w/M_n$ thereof.

When the mixtures of cyclically branched siloxanes having exclusively D and T units, as described above, have the feature that the branching T unit derives from alkyltrialkoxysilanes and/or, preferably or, phenyltrialkoxysilanes, this is a further preferred embodiment of the invention.

A preferred embodiment of the invention is likewise when the branching T unit derives from methyltriethoxysilane.

The aforementioned mixtures of the invention can especially be obtained via the process according to the invention for preparing mixtures of cyclic branched siloxanes having exclusively D and T units, comprising
(a) an acid-catalysed equilibration of trialkoxysilanes with siloxane cycles and/or α,ω-dihydroxypolydimethylsiloxane in the presence of at least one acidic catalyst and then
(b) a hydrolysis and condensation reaction initiated by addition of water, with subsequent use of a silicon-containing solvent, followed by
(c) a distillative removal of the alcohol released, of water present in the system and of silicon-containing solvent, and a neutralization or removal of the acidic catalyst and optionally removal of salts that have possibly formed.

The silicon-containing solvent preferably comprises the isomeric siloxane cycles octamethylcyclotetrasiloxane ($D_4$), decamethylcyclotetrasiloxane ($D_5$) and/or mixtures thereof, and it is advantageous to work in mass ratios of silicon-containing solvent to the siloxane having D and T units of 1:1 to 5:1. This corresponds to a preferred embodiment of the invention.

In a further preferred embodiment of the invention, the acidic catalyst used is para-toluenesulfonic acid, trifluoromethanesulfonic acid, trichloroacetic acid, sulfuric acid, perchloric acid, phosphoric acid and/or hexafluorophosphoric acid, preferably in amounts of 0.1 to 2.0 percent by weight, more preferably in amounts of 0.15 to 1.0 percent by weight, based in each case on the silicon-containing component of the reaction matrix.

In a further preferred embodiment of the invention, the acidic catalyst used is a macrocrosslinked ion exchange resin containing sulfonic acid groups, preferably in amounts of 1.0 to 10.0 percent by weight, more preferably in amounts of 2.0 to 6.0 percent by weight, based in each case on the silicon-containing component of the reaction matrix.

If the reaction according to the invention is conducted at temperatures in the range from 20° C. to 120° C., preferably from 40° C. to 110° C., this is a further preferred embodiment of the invention.

It is likewise a further preferred embodiment of the invention when an at least 150% excess of $H_2O$, preferably a 150% to 250% excess of $H_2O$, based on the groups to be condensed, is used.

If the reaction according to the invention comprises a preliminary equilibration step at temperatures of T>40° C., followed by a condensation initiated by addition of water at temperatures of T>60° C., where the water is added in one portion, in several portions or continuously, this is a further preferred embodiment of the invention.

For the process according to the invention, it is possible in principle to use any trialkoxysilanes. Trialkoxysilanes used may especially be those in which the alkoxy radicals are all the same or all different or in which some are the same. Trialkoxysilanes used may especially be triethoxysilanes, preferably methyltriethoxysilane, alkyltriethoxysilanes, for example n-propyltriethoxysilane, isobutyltriethoxysilane, pentyltriethoxysilane, hexyltriethoxysilane, octyltriethoxysilane, hexadecyltriethoxysilane, n-octadecyltriethoxysilane, halogenated or pseudohalogenated alkyltrialkoxysilanes, especially alkyltriethoxysilanes, for example chloropropyltriethoxysilane, tridecafluoro-1,1,2,2-tetrahydrooctyltriethoxysilane, nonafluoro-1,1,2,2-tetrahydrohexyltriethoxysilane, 3-cyanopropyltriethoxysilane, trialkoxysilanes, especially triethoxysilanes having functional groups, for example 3-methacryloyloxypropyltriethoxysilane, 3-mercaptopropyltriethoxysilane, 5-(bicycloheptenyl)triethoxysilane, phenyltriethoxysilane, (p-chloromethyl) phenyltriethoxysilane, N-(3-triethoxysilylpropyl)-4,5-dihydroimidazole or dihydro-3-[3-(triethoxysilyl)propyl]furan-2,5-dione. It may be advantageous for organically functionalized trialkoxysilanes to be used as branching unit (included in the equilibration).

Using the example of the D/T cycles derived from methyltriethoxysilane, a preferred process variant is as described by way of example hereinafter:

Preference is given in accordance with the invention to undertaking the equilibration of methyltriethoxysilane exclusively with siloxane cycles and/or α,ω-dihydroxypolydimethylsiloxane, with addition of a catalytic amount of preferably trifluoromethanesulfonic acid at 60° C. over the course of 2 to 4 hours, then, after adding a preferably 100% stoichiometric excess of water, conducting the condensation reaction over the course of preferably 2 to 4 hours at preferably 80° C., then preferably adding a portion of water to the system again, in order then to add a silicon-containing solvent, preferably simple siloxane cycles ($D_4/D_5$), and to conduct the distillative removal of ethanol-water mixtures until attainment of a bottom temperature of 90° C. and then optionally to leave the system at 90° C. for 2 to 4 hours. Thereafter, the system is cooled down and ammonia is preferably added, the mixture is stirred for a further 30 minutes for the purpose of neutralization, and residual water and the simple siloxane cycles ($D_4/D_5$) that do not contain T groups are distilled off, before separating the distillation residue from precipitated ammonium triflate by filtration.

The amount of water that has been introduced here into the system is preferably such that the total amount of water used over all the steps of the process according to the invention covers a stoichiometric excess of 150% to 500%, preferably 150% to 250%, based on methyltriethoxysilane used.

The trifluoromethanesulfonic acid, which is used with preference as equilibration catalyst in the process according to the invention, is preferably used in amounts of 0.1%-0.5% by weight, preferably in amounts of 0.15% to 0.3% by weight, based on the mass of the equilibration mixture.

In a completely surprising manner to the person skilled in the art, within the overall context of this invention, the simple siloxane cycles ($D_4/D_5$) added after the addition of water, in the subsequent distillation phase which is preferably conducted up to bottom temperature 90° C., advantageously function exclusively as a system-compatible solvent and not, for instance, as a co-reactant, and are therefore not incorporated into the D/T cycles in spite of their siloxane nature and the equilibrating acid still present in the system.

A crucial advantage of the preparation process according to the invention is that the synthesis of cyclic branched siloxanes can be conducted under more severe reaction conditions, for example at a high acid concentration and high temperatures, without product damage since there are no sensitive moieties present at all (for example SiH functions). Optimal incorporation of branching units (T structures) into the molecular skeletons of the siloxane oligomers is thus possible, where the T structures are ideally separated by D units in each case and are not present in cumulated form in a domain-like manner, as shown by the $^{29}$Si NMR spectroscopy, especially in the shift region of the T structures.

If desired, the reaction system can still be kept at 90° C. after distillative removal of the ethanol for another 2 to 4 hours. However, experiments demonstrate that the distillative removal of the ethanol-water mixtures can also be immediately followed by the cooling and neutralization phase without any impairment in the quality of the D/T cycles obtained by the process according to the invention, as demonstrated by the accompanying $^{29}$Si NMR analysis.

The ratio of D to T units is preferably between 10:1 and 3:1, preferably between 6:1 and 4:1. Depending on the desired D/T ratio, the amount of simple siloxane cycles ($D_4/D_5$) used as solvent is preferably such as to assure viscosities that can be handled in an efficient manner over the course of the reaction. Preferably, mass ratios of solvent to the siloxane of 0.5:1 to 5:1 are chosen. In accordance with economic considerations, it follows that, in industrial practice, a compromise will always be chosen between viscosities that can be handled in an efficient manner and the space-time yields achievable.

The silicon-containing solvents usable here with preference in accordance with the invention include the simple liquid dimethylsiloxane cycles such as octamethylcyclotetrasiloxane ($D_4$) and decamethylcyclopentasiloxane ($D_5$), and mixtures thereof. Particular preference is given to decamethylcyclopentasiloxane ($D_5$).

The importance of the simple siloxane cycles ($D_4/D_5$) added for the success of the process according to the invention becomes clear on the basis of the non-inventive comparison experiment (Example 2, cf. Experimental section), in which the addition thereof has been dispensed with.

The ammonia used with preference for neutralization is preferably added in the form of gaseous ammonia. If desired, however, it is also possible to use aqueous ammonia solutions.

If desired, the process according to the invention can also be modified to the effect that, after the process step in which the system is preferably left at 90° C. for another 2 to 4 hours, the water phase is removed after cooling and the siloxane phase is neutralized with sodium hydrogencarbonate, the salt is filtered off and the simple non-T-group-containing siloxane cycles ($D_4/D_5$) are distilled off.

In principle, it is also possible to use other bases, for example organic amines, for neutralization of the trifluoromethanesulfonic acid present in the system. Preference is given to using ammonia in the form of aqueous solutions. Especially from the point of view of industrial production, however, particular preference is given to using gaseous ammonia.

If, in a further preferred embodiment of the invention, the acidic catalyst used is a macrocrosslinked ion exchange resin containing sulfonic acid groups, the neutralization initiated with addition of base is replaced by the simple removal of the resin by filtration, for example.

It is possible to isolate mixtures of cyclic branched siloxanes in virtually quantitative yields, these being clear colorless liquids of low viscosity, the corresponding $^{29}$Si NMR spectrum of which demonstrates the dominant presence of D and T units. The cumulative contents of D and T units having Si-alkoxy and SiOH groups determined by $^{29}$Si NMR spectroscopy, in the cyclic branched siloxanes of the D/T type obtained by the process according to the invention, are greater than 2 mole percent. The Si-alkoxy and SiOH contents are preferably within a concentration range from 3 to 8 mole percent, preferably within a concentration range from 3 to 5 mole percent, based on the totality of silicon detected by spectroscopy.

The concentration range for the groups capable of condensation (Si-alkoxy and SiOH) specified here which is preferred in accordance with the invention derives from the technical complexity involved in processing cyclic branched siloxanes of the D/T type that have been prepared in accordance with the invention to give functionalized branched siloxanes and/or branched silicone oils.

As disclosed in Example 4, it is possible in accordance with the invention to process cyclic branched siloxanes of the D/T type that have been prepared in simple siloxane cycles ($D_4/D_5$) and have a proportion of Si-alkoxy and SiOH, determined by spectroscopy, of 3 to 5 mole percent, based on the totality of silicon detected by spectroscopy, without adjustment of the standard equilibration conditions (0.1% by weight of added trifluoromethanesulfonic acid, 40° C.≤reaction temperature≤60° C., reaction time 6 hours), to give the corresponding functionalized branched siloxanes and/or branched silicone oils, which corresponds to a further preferred embodiment of the process of the invention.

Higher proportions of Si-alkoxy and SiOH lead to an adjustment of the standard equilibration conditions to the effect that, for example, the added amount of trifluoromethanesulfonic acid is slightly increased (from 0.1% by weight, for example, to 0.2% by weight, Example 6) and/or else the time-limited application of an auxiliary vacuum in the equilibration step lowers the concentration of the groups capable of condensation (Example 5), which corresponds to a further preferred embodiment of the process according to the invention.

A further course of action preferred in accordance with the invention is to combine the time-limited application of an auxiliary vacuum with the sequenced addition of the amount of trifluoromethanesulfonic acid to be used (Example 7), which likewise corresponds to a further preferred embodiment of the invention. This process variant makes it possible to leave the amount of trifluoromethanesulfonic acid at the level of the standard equilibration conditions (0.1% by weight).

A process according to the invention as described above in which, thus, in the second step in which the mixtures of cyclic branched siloxanes are acid-equilibrated with silanes and/or siloxanes, (a) an amount of ≥0.2% by weight of acidic catalyst, preferably trifluoromethanesulfonic acid, is used,
(b) the preferably time-limited application of an auxiliary vacuum in the equilibration step lowers the concentration of the groups capable of condensation, and/or
(c) there is sequenced addition of the acidic catalyst, preferably trifluoromethanesulfonic acid, and/or
(d) steps (b) and (c) are combined, corresponds to a preferred embodiment of the invention, which is particularly preferred in turn when the mixtures of cyclic branched siloxanes having exclusively D and T units that are produced in the first step fulfil the proviso that the cumulative proportion of the D and T units having Si-alkoxy and/or SiOH groups that are present in the siloxane matrix, determinable by $^{29}$Si NMR spectroscopy, is greater than 5 and less than 10 mole percent, preferably less than 9 mole percent.

In this context, the auxiliary vacuum applied is preferably ≤200 mbar, preferably ≤150 mbar, and/or the sequenced addition of the acidic catalyst is preferably effected in 2 steps.

A further embodiment of the process claimed which is preferred in accordance with the invention arises from the use of a water-containing macroporous polystyrene resin containing sulfonic acid groups, for example of a Lewatit® K 2621 wetted with 10% by weight of water. If this resin is added, for example, in amounts of about 6% by weight to the reaction system as catalyst, the product obtained after a reaction conducted at about 40° C. over the course of 6 hours does not have any proportions of SiOH or SiOR groups at all, based on the total silicon detected by $^{29}$Si NMR spectroscopy (Example 8).

A process according to the invention as described above in which, thus, in the second step in which the mixtures of cyclic branched siloxanes are acid-equilibrated with silanes and/or siloxanes and the equilibration is undertaken over a water-containing macroporous polystyrene resin containing sulfonic acid groups, which is preferably used in amounts of 3% to 9% by weight based on the mixture to be equilibrated, and which has preferably been wetted with 8% to 12% by weight of water, and the specific surface area of which is preferably ≥35 m$^2$/g and the mean pore diameter of which is preferably at least 65 nm, corresponds to a particularly preferred embodiment of the invention.

An example of a particularly preferred cation exchange resin containing sulfonic acid groups is Lewatit® K 2621.

To achieve the final siloxane structure, acidic equilibration with silanes, preferably functional silanes, and/or siloxanes is conducted.

This corresponds to the process according to the invention for preparing branched organomodified siloxanes, wherein in a first step mixtures of cyclic branched siloxanes are provided, preferably as described above in detail, especially according to any of Claims 1 to 11, and in a second step the mixtures of cyclic branched siloxanes are equilibrated under acidic conditions with silanes and/or siloxanes.

The silanes and/or siloxanes used may be any acid-equilibratable silicon compounds. Functional silanes and/or siloxanes are preferred.

Functional silane/siloxane are understood in this connection to mean all those compounds comprising one silicon atom and/or multiple silicon atoms which can be incorporated into the copolymer by way of acidic equilibration. More particularly, these acid-equilibratable silanes/siloxanes, as well as any hydrogen, alkyl or aryl, or vinyl substituents present, also have hydroxyl, alkoxy and chlorine substituents. Likewise suitable are functional silanes/siloxanes that bear acidic moieties, for example toluenesulfonate, trifluoromethylsulfonate and sulfate radicals.

The silanes used may especially be diethoxydimethylsilane, trimethylalkoxysilanes and/or dimethyldichlorosilane.

The siloxanes used may especially be tetramethyldisiloxane, α,ω-dihydropolydimethylsiloxanes, poly(methylhydro)siloxanes, α,ω-dialkoxypolydimethylsiloxanes and/or α,ω-divinylpolydimethylsiloxanes.

As a special case, branched silicone oils are obtainable by the acidic co-equilibration of the cyclic branched siloxane of the D/T type obtained in the first step with hexamethyldisiloxane and/or polydimethylsiloxanes.

This corresponds to the process according to the invention for preparing branched silicone oils, wherein in a first step cyclic branched siloxanes are provided, preferably as stipulated in any of Claims 1 to 11, and in a second step the cyclic branched siloxanes are reacted with polydimethylsiloxanes or hexamethyldisiloxane.

Suitable acidic catalysts are the strong acids (equilibrating acids) known from the prior art for siloxanes, i.e. mineral acids, for example sulfuric acid, but also sulfonic acids, fluoroalkylsulfonic acids, for example trifluoromethanesulfonic acid, acidic aluminas or acidic ion exchange resins, for example the products known by the Amberlite®, Amberlyst® or Dowex® and Lewatit® brand names.

In the process according to the invention, it is possible to use either natural ion exchangers, for example zeolites, montmorillonites, attapulgites, bentonites and other aluminosilicates, or synthetic ion exchangers. The latter are preferably solids (usually in granular form) with a three-dimensional, water-insoluble, high molecular weight matrix based on phenol-formaldehyde resins or copolymers of styrene-divinylbenzene into which numerous "anchor groups" of different acidity have been incorporated.

Acidic ion exchangers used advantageously may include those as described in EP 1439200 B1.

Preference is given to using sulfonic acid catalysts and very particular preference to using trifluoromethanesulfonic acid.

Gas chromatography analysis shows that, typically, simple siloxane cycles such as $D_4$ (octamethylcyclotetrasiloxane), $D_5$ (decamethylcyclopentasiloxane) and $D_6$ (dodecamethylcyclohexasiloxane) are present in the equilibrates only in proportions by weight of less than 10%.

If desired for the respective later application (for example within the scope of the VOC discussion (VOC=volatile organic compounds) or of anti-fogging), these siloxane cycles can be removed by simple distillation and recycled.

It will be immediately apparent to the person skilled in the art that the branched organomodified siloxanes obtained by acidic equilibration from the second step are suitable as starting material for production of stabilizers for PUR foams, for production of defoamers, for production of paint additives, for production of emulsifiers, especially of cosmetic emulsifiers, for production of cosmetic conditioners, for production of deaerating agents, for production of demulsifiers, for production of textile finishes, for production of building protection additives, for production of polymer additives, especially anti-scratch additives, for production of antifouling additives or coatings, and for production of anti-icing coatings. This use forms a further part of the subject-matter of the present invention.

Depending on the SiH group or functionality (e.g. SiH group) incorporated in the second step (e.g. SiH group or SiCl group), for all these aforementioned applications, after selection of appropriate co-reactants, SiC-bonded final products are obtainable via hydrosilylation, or else SiOC-bonded final products are obtainable via dehydrogenative SiOC bond formation or condensation by the known methods of silicone chemistry.

The $^{29}$Si NMR samples, in the context of this invention, are analysed at a measurement frequency of 79.49 MHz in a Bruker Avance III spectrometer equipped with a 287430 sample head with gap width 10 mm, dissolved at 22° C. in $CDCl_3$ and against tetramethylsilane (TMS) as external standard [δ($^{29}$Si)=0.0 ppm].

The weight-average molar mass $M_w$ and the molar mass distribution $M_w/M_n$ are determined in the context of this invention using an EcoSEC GPC/SEC instrument from TOSOH Bioscience GmbH by gel permeation chromatography from toluenic solutions of the siloxanes. A Micro SDV 1000/10000 column of length 55.00 cm is used, combined with an EcoSEC RI detector (dual flow refractive index detection). The polystyrene standard covers the molar mass range from 162 g/mol to 2 520 000 g/mol.

EXAMPLES

1) Preparation of a Cyclic Branched Siloxane Having a Target D/T Ratio of 6:1 (Inventive)

In a 500 ml four-neck round-bottom flask with a precision glass stirrer and a reflux condenser on top, 52.2 g (0.293 mol) of methyltriethoxysilane are heated to 60° C. together with 130.3 g (0.351 mol) of decamethylcyclopentasiloxane while stirring, 0.400 g of trifluoromethanesulfonic acid is added and the mixture is equilibrated for 4 hours. Then 15.8 g of water and 4.0 g of ethanol are added and the mixture is heated to reflux temperature (about 80° C.) for a further 4 hours. 10.6 g of water and 200 ml of decamethylcyclopentasiloxane ($D_5$) are added and the reflux condenser is exchanged for a distillation system, and the constituents that are volatile up to 90° C. are distilled off within the next hour. The reaction mixture is left at 90° C. for a further 2 hours, then allowed to cool down to 50° C., and 5 ml of a 25% aqueous ammonia solution are added and the mixture is stirred for a further hour to complete the neutralization. At 100° C. and with an auxiliary vacuum of <1 mbar applied, water and the decamethylcyclopentasiloxane ($D_5$) used as solvent are distilled off. After cooling the distillation bottoms, with the aid of a fluted filter, the precipitated ammonium triflate is removed. The filtrate is a colorless mobile liquid, the $^{29}$Si NMR spectrum of which shows a D/T ratio of 6.1:1 (target: 6.0:1). Based on the sum total of the Si units detected by spectroscopy, the D and T units bearing Si-alkoxy and SiOH groups respectively, have a proportion of 4.1 mole percent.

The siloxane showed excellent storage stability, even when stored under air and at high temperatures. Solidification or even through-curing did not occur, even after storage under air at elevated temperatures for a number of months.

2) Preparation of a Cyclic Branched Siloxane Having a Target D/T Ratio of 6:1 (Non-Inventive)

In a 500 ml four-neck round-bottom flask with a precision glass stirrer and a reflux condenser on top, 52.2 g (0.293 mol) of methyltriethoxysilane are heated to 60° C. together with 130.3 g (0.351 mol) of decamethylcyclopentasiloxane while stirring, 0.400 g of trifluoromethanesulfonic acid is added and the mixture is equilibrated for 4 hours. Then 15.8 g of water and 4.0 g of ethanol are added and the mixture is heated to reflux temperature (about 80° C.) for a further 4 hours. 10.6 g of water are added and the reflux condenser is exchanged for a distillation system, and the constituents that are volatile up to 90° C. are distilled off within the next hour. A significant increase in viscosity accompanied by foam formation are the initial stages of the complete gelation of the reaction mixture.

3) Preparation of a Cyclic Branched Siloxane Having a Target D/T Ratio of 6:1 (Inventive)

In a 10l four-neck round-bottom flask with a precision glass stirrer and a reflux condenser on top, 783 g (4.39 mol) of methyltriethoxysilane are heated to 60° C. together with 1957.5 g (5.279 mol) of decamethylcyclopentasiloxane while stirring, 5.95 g (0.2%) of trifluoromethanesulfonic acid are added and the mixture is equilibrated for 4 hours. Then 237 g of water and 59.3 g of ethanol are added and the mixture is heated to reflux temperature (about 80° C.) for a further 4 hours. 78.9 g of water and 3000 ml of decamethylcyclopentasiloxane ($D_5$) are added and the reflux condenser is exchanged for a distillation system, and the constituents that are volatile up to 90° C. are distilled off within the next hour. Then the mixture is allowed to cool down to 60° C., and 11.5 g of a 25% aqueous ammonia solution are added and the mixture is stirred for a further hour to complete the neutralization. At 70° C. and with an auxiliary vacuum of <1 mbar applied, first water is distilled off and then, after increasing the bottom temperature to 130° C., the decamethylcyclopentasiloxane ($D_5$) used as solvent. After cooling the distillation bottoms, with the aid of a fluted filter, the precipitated ammonium triflate is removed.

The filtrate is a colorless mobile liquid, the $^{29}$Si NMR spectrum of which shows a D/T ratio of 5.8:1 (target: 6.0:1). Based on the sum total of the Si units detected by spectroscopy, the D and T units bearing Si-alkoxy and SiOH groups respectively, have a proportion of 7.8 mole percent. This siloxane too showed excellent storage stability as in Example 1).

4) Preparation of a Branched Hydrosiloxane Having Terminal SiH Functions from the Cyclic Branched Siloxane from Example 1 with α,ω-Dihydropolydimethylsiloxane and Decamethylcyclopentasiloxane (Inventive)

32.5 g of the cyclically branched siloxane prepared in Example 1 are heated to 40° C. together with 26.2 g of an α,ω-dihydropolydimethylsiloxane (SiH value: 2.90 eq/kg) and 191.3 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top for 6 hours, then 5 g of sodium hydrogencarbonate are added and the mixture is stirred for a further 30 minutes. With the aid of a filter press (Seitz K 300 filter disc), the salt is separated from the equilibrate.

What is obtained is a colorless branched hydrosiloxane having dimethylhydrosiloxy functions in its termini (SiH value: 0.30 eq/kg) and a viscosity of 145 mPas (25° C., Höppler viscometer). The corresponding $^{29}$Si NMR spectrum confirms the target structure.

5) Preparation of a Branched Hydrosiloxane Having Terminal SiH Functions from the Cyclic Branched Siloxane from Example 3 with α,ω-Dihydropolydimethylsiloxane and Decamethylcyclopentasiloxane (Inventive)

29.2 g of the cyclically branched siloxane prepared in Example 3 are heated to 40° C. for 6 hours, with application of an oil-pump vacuum of 100 mbar, together with 26.3 g of an α,ω-dihydropolydimethylsiloxane (SiH value: 2.90 eq/kg) and 194.5 g of decamethylcyclopentasiloxane with addition of 0.25 g of trifluoromethanesulfonic acid (0.1 m % based on the overall mixture) in a 500 ml four-neck flask with precision glass stirrer and a reflux condenser on top. After the auxiliary vacuum has been broken, 5 g of sodium hydrogencarbonate are then added to the mixture which is stirred for a further 30 minutes. With the aid of a filter press (Seitz K 300 filter disc), the salt is separated from the equilibrate.

What is obtained is a colorless branched hydrosiloxane having dimethylhydrosiloxy functions in its termini (SiH value: 0.31 eq/kg) and a viscosity of 156 mPas (25° C., Höppler viscometer).

6) Preparation of a Branched Hydrosiloxane Having Terminal SiH Functions from the Cyclic Branched Siloxane from Example 3 with α,ω-Dihydropolydimethylsiloxane and Decamethylcyclopentasiloxane (Inventive)

29.2 g of the cyclically branched siloxane prepared in Example 3 are heated to 40° C. together with 26.3 g of an α,ω-dihydropolydimethylsiloxane (SiH value: 2.90 eq/kg) and 194.5 g of decamethylcyclopentasiloxane with addition of 0.5 g of trifluoromethanesulfonic acid (0.2 m % based on the overall mixture) in a 500 ml four-neck flask with precision glass stirrer and a reflux condenser on top for 6 hours, then 10 g of sodium hydrogencarbonate are added and the mixture is stirred for a further 30 minutes. With the aid of a filter press (Seitz K 300 filter disc), the salt is separated from the equilibrate.

What is obtained is a colorless branched hydrosiloxane having dimethylhydrosiloxy functions in its termini (SiH value: 0.29 eq/kg) and a viscosity of 149 mPas (25° C., Höppler viscometer).

7) Preparation of a Branched Hydrosiloxane Having Terminal SiH Functions from the Cyclic Branched Siloxane from Example 3 with α,ω-Dihydropolydimethylsiloxane and Decamethylcyclopentasiloxane (Inventive)

29.2 g of the cyclically branched siloxane prepared in Example 3 are heated to 40° C. for 1 hour, with application of an oil-pump-generated auxiliary vacuum of 100 mbar, together with 26.3 g of an α,ω-dihydropolydimethylsiloxane (SiH value: 2.90 eq/kg) and 194.5 g of decamethylcyclopentasiloxane with addition of 0.08 g of trifluoromethanesulfonic acid (0.033 m % based on the overall mixture) in a 500 ml four-neck flask with precision glass stirrer and a reflux condenser on top. The auxiliary vacuum is then broken and a further 0.17 g of trifluoromethanesulfonic acid (0.067 m % based on the overall mixture) is added. The mixture is left to react at 40° C. without application of an auxiliary vacuum for a further 6 hours. 5 g of sodium hydrogencarbonate are added and the mixture is left to stir for a further 30 minutes, and then the salt is separated from the equilibrate with the aid of a filter press (Seitz K 300 filter disc).

What is obtained is a colorless branched hydrosiloxane having dimethylhydrosiloxy functions in its termini (SiH value: 0.29 eq/kg) and a viscosity of 142 mPas (25° C., Höppler viscometer).

8) Preparation of a Branched Hydrosiloxane Having Terminal SiH Functions from the Cyclic Branched Siloxane from Example 3 with α,ω-Dihydropolydimethylsiloxane and Decamethylcyclopentasiloxane (Inventive)

29.2 g of the cyclically branched siloxane prepared in Example 3 are heated to 40° C. for 6 hours together with 26.3 g of an α,ω-dihydropolydimethylsiloxane (SiH value: 2.90 eq/kg) and 194.5 g of decamethylcyclopentasiloxane with addition of 15 g of predried Lewatit K2621 (water content 10% by weight, 6% by weight based on the overall mixture) in a 500 ml four-neck flask with precision glass stirrer and a reflux condenser on top, and then the ion exchange resin is separated from the equilibrate with the aid of a filter press (Seitz K 300 filter disc).

What is obtained is a colorless branched hydrosiloxane having dimethylhydrosiloxy functions in its termini (SiH value: 0.30 eq/kg) and a viscosity of 152 mPas (25° C., Höppler viscometer), which does not have any fractions at all of SiOH or SiOR groups, based on the total silicon detected by $^{29}$Si NMR spectroscopy.

The invention claimed is:

1. A mixture of cyclic branched siloxanes having exclusively D and T units, wherein the cumulative proportion of the D and T units having Si-alkoxy and/or SiOH groups that are present in the siloxane matrix, determinable by $^{29}$Si NMR spectroscopy, is greater than 2 and less than 10 mole percent, wherein the cyclic branched siloxanes do not have any further functional groups.

2. The mixture of cyclic branched siloxanes according to claim 1, wherein the ratio of D to T units is between 10:1 and 3:1.

3. The mixture of cyclic branched siloxanes having exclusively D and T units according to claim 1, wherein the molar mass ratio of the mixture $M_w/M_n$ is in the range of $2<M_w/M_n<50$.

4. The mixture of cyclic branched siloxanes according to claim 1, wherein the branching T unit derives from alkyltrialkoxysilanes and phenyltrialkoxysilanes.

5. The mixture of cyclic branched siloxanes according to claim 1, wherein the branching T unit derives from methyltriethoxysilane.

6. The mixture of cyclic branched siloxanes according to claim 1, dissolved in a silicon-containing solvent.

7. The process for preparing mixtures of cyclic branched siloxanes according to claim 1, comprising (a) an acid-catalysed equilibration of trialkoxysilanes with siloxane cycles and/or α,ω-dihydroxypolydimethylsiloxane in the presence of at least one acidic catalyst and then (b) a hydrolysis and condensation reaction initiated by addition of water, and addition of a silicon-containing solvent, followed by (c) a distillative removal of the alcohol released, of water present in the system and of silicon-containing solvent, and a neutralization or removal of the acidic catalyst and optionally removal of salts that have possibly formed, wherein the silicon-containing solvent preferably comprises the isomeric siloxane cycles octamethylcyclotetrasiloxane ($D_4$), decamethylcyclotetrasiloxane ($D_5$) and/or mixtures thereof, advantageously working in mass ratios of silicon-containing solvent to the siloxane having D and T units of from 1:1 to 5:1.

8. The process according to claim 7, wherein the acidic catalyst used is para-toluenesulfonic acid, trifluoromethanesulfonic acid, trichloroacetic acid, sulfuric acid, perchloric acid, phosphoric acid and/or hexafluorophosphoric acid, in amounts of from 0.1 to 2.0 percent by weight, based in each case on the silicon-containing component of the reaction matrix.

9. The process according to claim 8, wherein the reaction is conducted at temperatures in the range from 20° C. to 120° C.

10. The process according to claim 7, wherein the acidic catalyst used is a macrocrosslinked ion exchange resin containing sulfonic acid groups in amounts of from 1.0 to 10.0 percent by weight based in each case on the silicon-containing component of the reaction matrix.

11. The process according to claim 7, wherein an at least 150% $H_2O$ excess is used, based on the groups to be condensed.

12. The process according to claim 1, wherein the reaction comprises a preliminary equilibration step at temperatures of T>40° C., followed by a condensation initiated by addition of water at temperatures of T>60° C., where the water is added in one portion, in several portions or continuously.

13. The process for preparing branched organomodified siloxanes, wherein in a first step mixtures of cyclic branched siloxanes are provided according to claim 1,
and
in a second step the mixtures of cyclic branched siloxanes are equilibrated under acidic conditions with silanes and/or siloxanes.

14. The process according to claim 13, wherein the silanes and/or siloxanes used are acid-equilibratable silicon compounds, wherein the silanes are selected from the group consisting of diethoxydimethylsilane, trimethylalkoxysilanes and dimethyldichlorosilane,
and/or
wherein the siloxanes are selected from the group consisting of tetramethyldisiloxane, α,ω-dihydropolydimethylsiloxanes, poly(methylhydro)siloxanes, α,ω-dialkoxypolydimethylsiloxanes and α,ω-divinylpolydimethylsiloxanes.

15. The process according to claim 13, wherein, in the second step in which the mixtures of cyclic branched siloxanes are acid-equilibrated with silanes and/or siloxanes, a) an amount of ≥0.2% by weight of acidic catalyst,
b) the preferably time-limited application of an auxiliary vacuum in the equilibration step lowers the concentration of the groups capable of condensation, where the auxiliary vacuum is ≤200 mbar, and/or c) there is sequenced addition of the acidic catalyst, the sequenced addition preferably being effected in 2 steps, and/or d) steps (b) and (c) are combined.

16. The process according to claim 13, wherein in the second step in which the mixtures of cyclic branched siloxanes are acid-equilibrated with silanes and/or siloxanes, the equilibration is undertaken over a water-containing macroporous polystyrene resin containing sulfonic acid groups, which is used in amounts of 3% to 9% by weight and which has been wetted with 8% to 12% by weight of water, and the specific surface area of which is ≥35 $m^2/g$ and the mean pore diameter of which is at least 65 nm.

17. The process for preparing branched silicone oils, wherein in a first step cyclic branched siloxanes are provided, according to claim 1, and in a second step the cyclic branched siloxanes are reacted with polydimethylsiloxanes or hexamethyldisiloxane.

18. The mixture of cyclic branched siloxanes according to claim 1, wherein the cumulative proportion of the D and T units having Si-alkoxy and/or SiOH groups that are present in the siloxane matrix, determinable by $^{29}Si$ NMR spectroscopy, is less than 9 mole percent.

19. The mixture of cyclic branched siloxanes according to claim 1, wherein the ratio of D to T units is between 6:1 and 4:1.

20. The mixture of cyclic branched siloxanes having exclusively D and T units according to claim 1, dissolved in isomeric siloxane cycles octamethylcyclotetrasiloxane $D_4$, decamethylcyclotetrasiloxane $D_5$ or mixtures thereof.

\* \* \* \* \*

UNITED STATES PATENT AND TRADEMARK OFFICE
CERTIFICATE OF CORRECTION

PATENT NO. : 10,399,998 B2
APPLICATION NO. : 15/923552
DATED : September 3, 2019
INVENTOR(S) : Wilfried Knott and Horst Dudzik Page 1 of 1

It is certified that error appears in the above-identified patent and that said Letters Patent is hereby corrected as shown below:

In the Claims

Column 15,
Lines 54-55, Claim 3, "branched siloxanes having exclusively D and T units according to claim 1" should read -- branched siloxanes according to claim 1 --.

Signed and Sealed this
First Day of October, 2019

Andrei Iancu
*Director of the United States Patent and Trademark Office*